United States Patent [19]
Yesair

[11] Patent Number: 5,972,911
[45] Date of Patent: Oct. 26, 1999

[54] COMPOSITION FOR THE DELIVERY OF ORALLY ADMINISTERED DRUGS AND OTHER SUBSTANCES

[76] Inventor: David W. Yesair, P.O. Box 347, Byfield, Mass. 01922

[21] Appl. No.: 07/890,384

[22] Filed: May 26, 1992

Related U.S. Application Data

[63] Continuation of application No. 07/378,388, Jul. 11, 1989, abandoned, which is a continuation of application No. 06/843,058, Mar. 24, 1986, Pat. No. 4,874,795, which is a continuation-in-part of application No. 06/718,876, Apr. 2, 1985, abandoned.

[51] Int. Cl.$^6$ .......................... A61K 31/685; A61K 31/20
[52] U.S. Cl. ........................... 514/77; 514/558; 514/560; 514/946; 514/947
[58] Field of Search .............................. 514/77, 558, 560, 514/946, 947

[56] References Cited

U.S. PATENT DOCUMENTS

| | | | |
|---|---|---|---|
| 3,090,725 | 5/1963 | Copp et al. | 167/55 |
| 4,263,313 | 4/1981 | Eckert et al. | 424/273 |
| 4,324,797 | 4/1982 | Suzuki | 424/287 |
| 4,485,033 | 11/1984 | Kitao et al. | 252/315.4 |
| 4,810,697 | 3/1989 | Speiser et al. | 514/77 |
| 4,874,795 | 10/1989 | Yesair | 514/725 |

FOREIGN PATENT DOCUMENTS

| | | |
|---|---|---|
| 0023349 | 2/1981 | European Pat. Off. |
| 2427100 | 12/1979 | France |
| 286061 | 2/1913 | Germany |
| 1085328 | 4/1986 | Japan |
| 83/00294 | 2/1983 | WIPO |

OTHER PUBLICATIONS

Physicians Desk Reference for Non Prescription Drugs 3rd Ed 1982, p. 564.
Merck index 10$^{th}$ Ed # 5271+7395.
The Merck Index (Merck and Co., Rahway, N.J., 1989) p. 172.
Yesair, Phospholipids, Plenum Press, 1990 p. 83 and 100.
Frank, Journal of Pharmaceutical Sciences 64(10), 1975 pp. 1585–1603.
Muranishi, S. et al., *International Journal of Pharmaceutics*, 2:101–111 (1979).
Muranishi, S. et al., *Journal of Pharmaceutic Dynamics*, 2:286–294 (1979).
Muranishi, N. et al., *International Journal of Pharmaceutics*, 4:271–279 (1980).
Taniguchi, K. et al., *International Journal of Pharmaceutics*, 4:219–228 (1980).
Padfield, J.M. and I.W. Kellaway, *Journal of Pharmacy and Pharmaceuticals*, 24 (Suppl.): 171P (1972).
Serajuddin, A.T.M. et al., *Pharmaceutical Research*,__:221–224 (1985).
Yoshikawa, H. et al., *Pharmaceutical Research*,__:249–250 (1985).
Muranishi, S., *Pharmaceutical Research*, __ :108–118 (1985).

*Primary Examiner*—Russell Travers
*Attorney, Agent, or Firm*—Wolf, Greenfield & Sacks, P.C.

[57] ABSTRACT

A composition comprised of non-esterified fatty acids having 14–18 carbon atoms; monoglycerides which are monoesters of glycerol and fatty acids having 14–18 carbon atoms; lysophosphatidyl choline in which the fatty acid moiety has 14–18 carbon atoms and a drug is disclosed. The composition is useful for the delivery of orally-administered drugs. The composition is also useful as a source of readily absorbable fat. When used in this manner, the composition is comprised of non-esterified fatty acids having 14–18 carbon atoms; monoglycerides which are monoesters of glycerol and fatty acids having 14–18 carbon atoms; lysophosphatidyl choline in which the fatty acid moiety has 14–18 carbon atoms. A method of making the compositions disclosed is also described.

2 Claims, 2 Drawing Sheets

COMPOSITION FOR THE DELIVERY OF ORALLY ADMINISTERED DRUGS AND OTHER SUBSTANCES

RELATED APPLICATION

This is a continuation of application Ser. No. 07/378,388 filed on Jul. 11, 1989, now abandoned which is a continuation of Ser. No. 06/843,058 filed Mar. 24, 1986 U.S. Pat. No. 4,879,795 which is a continuation-in-part of 06/718,876 filed Apr. 2, 1985, now abandoned.

DESCRIPTION

1. Technical Field

This invention is in the field of biology and in particular relates to lipid compositions for the delivery and release of drugs and other substances via the lymphatics into the systemic circulation.

2. Background Art

Drug Absorption

Drugs must reach their targets selectively and controllably if their desired pharmacological activities are to be maximized. One approach to optimizing the activities of drugs is their controlled and sustained delivery into the systemic circulation. Orally administered drugs are generally absorbed in the intestine. Such drugs undergo first pass clearance by the liver and small intestine; that is, they are converted by the intestine and the liver to pharmacologically inactive metabolites and/or are secreted into bile by the liver, either as drug or as active metabolites. As a result, the amount of an orally administered drug actually entering the systemic circulation can be much less than the amount administered. To ensure that effective quantities of such a drug will enter the circulation and reach the targeted site(s) in the body, larger quantities than actually needed must be administered and often must be given in several smaller doses, rather than one dose. Orally administered drugs also typically have poor bio-availability. For example, they may be adversely affected by the pH and the enzymatic activity of the stomach and intestine and may be poorly dissolved in the stomach and intestinal fluids.

There have been numerous attempts to address these problems and to improve the bioavailability of orally administered drugs. The efficacy of some drugs given orally has been improved by administering them with a triglyceride or neutral fat. Such fats represent an environment that is compatible with lipophilic drugs, i.e. they exhibit low aqueous solubility. Fats also enhance the stability of drugs which are unstable in the stomach and intestine. The end products of fat digestion are absorbed by the villi of the intestinal mucosa into a lymphatic vessel, the central lacteal; absorption occurs within a region of the intestine in which limited drug metabolism occurs. The absorbed fat is transported through the thoracic duct, the major lymphatic channel and is subsequently emptied into the blood; it is not carried in the portal blood, which goes to the liver, where first pass metabolism of drugs occurs.

The absorption of griseofulvin has been shown to be enhanced if the drug is co-administered with a high fat content meal or in an oil and water emulsion. Crounse, R. G., *Journal of Investigative Dermatology,* 37: 529 (1961); Carrigan, P. J. and Bates, T. R., *Journal of Pharmacological Science,* 62: 1476 (1973). If the hormone testosterone undecanoate is administered in a peanut oil solution, it is more biologically active than if it is administered in an aqueous micro-crystalline suspension. Coert, A. J. et al., *Acta Endocrinol,* 79: 789, (1975);Hirschhauser, C. et al., *Acta Endocrinol.,* 80: 179. (1975). This effect is presumed to be due to absorption of the steroid via the thoracic lymph rather than the portal blood; in this way, first pass clearance by the liver is avoided.

Cholesterol, its esters and triglyceride constituents (e.g., fatty acids and monoglycerides) are absorbed via the thoracic lymph. The effects of some of these compounds, alone or in the presence of bile salts, upon absorption of some orally administered drugs have been evaluated. For example, oral administration of ubidecarenone, which is used for treating hypertension, in a mixture containing fatty acids having 12 to 18 carbon atoms and monoglycerides containing such fatty acids, resulted in somewhat greater absorption of the ubidecarenone than occurred after oral administration of the drug alone (8.3% v. 2.3%). Taki, K. and Takahira, H., U.S. Pat. No. 4,325,942. (1982). If the steroid progesterone is administered orally in combination with cholesterol or its esters, good sustained biological activity can be obtained. This is believed to be due to the absorption of progesterone via the thoracic lymph and not via the portal circulation. Kincl, F. A., *Proceedings of the 6th International Congress of Pharmacology,* 5: 105, (1975).

Yesair has evaluated the effect of fatty acids having 12 to 18 carbon atoms, monoglycerides of these fatty acids, and bile salts on the absorption of orally administered estradiol, which is an estrogenic hormone. Yesair, D. W., PCT WO 83/00294 (1983). The mole ratio of fatty acids: monoglycerides: bile salts evaluated ranged from 10:1:1, 1:1:10 or 1:10:1. The preferred ratio is stated to be 2:1:2, which is similar to the micellar composition resulting from the enzymatic digestion of triglycerides in the intestine, which occurs in the presence of bile salts and calcium ions. When excess bile salts are present, estradiol incorporated into the 2:1:2 composition can migrate or partition into a bile salt-enriched micellar solution. This migration or partitioning of estradiol occurred prior to absorption of the drug, as shown by the fact that the initial concentrations in plasma of estradiol are initially greater than those in lymph. In addition, about 25–50% of the estradiol administered in the composition was co-absorbed with the lipid constituents and entered the systemic circulation via the thoracic lymph.

The presence of bile salts, which are absorbed in the ileum (and not in the jejunum, as is most fat) compromised the co-absorption of estradiol with fat by enhancing the migration of the drug from fat to the bile salt micelle. Phosphatidyl choline was used in an effort to maintain the estradiol within the micellar composition in which fatty acids: monoglycerides:bile salts occurred in a 2:1:2 molar ratio. In the presence of excess bile salts, about 60% of the estradiol incorporated into the 2:1:2 micellar composition remained associated with it when phosphatidyl choline was not present. Under the same conditions, about 70–75% of the estradiol remained in the composition when phosphatidyl choline was used. Addition of phosphatidyl choline for this purpose, however, results in an increased size of the delivery system. Size is an important parameter in the absorption of lipid micelles and this effect of phosphatidyl choline might interfere with co-absorption of the drug with the lipids. In addition, excess phosphatidyl choline has been shown to reduce lipid absorption. Ammon, H. V. et al., *Lipids,* 14: 395 (1979); Clark, S. B., *Gastro-intestinal Physiology,* 4: E183 (1978).

Others have also described the effects of the presence of bile salts in lipid formulations used for co-absorption of drugs. Wilson, T. H., *In: Intestinal Absorption,* Saunders, (1962); Lack, L. and Weiner, I. M., *American Journal of*

Physiology, 240: 313, (1961); H. V. Ammon et al, Lipids, 14: 395, (1979). For example, little difference in the absorption of 5-fluorouracil (5FU) in the stomach or small intestine was evident when the 5FU was administered alone or in a mono-olein/sodium taurocholate mixed micelle formulation. 5FU absorption in the large intestine was greater when the drug was administered in the formulation than when it was administered alone. Streptomycin is poorly absorbed from the intestine. Muranushi and co-workers report that mixed micelles, composed of bile salts, mono-olein or unsaturated fatty acids, did not improve the absorption of streptomycin from the small intestine but markedly enhanced the absorption from the large intestine. The enhancement in the large intestine was attributed mostly to the alteration of the mucosal membrane permeability by mono-olein or unsaturated fatty acids. In contrast, mixed micelles of bile salts and saturated fatty acids produced only a small enhancement in streptomycin absorption even from the large intestine. Muranushi, N. et al., *Journal of Pharmaceutics*, 4: 271 (1980). Taniguchi et al. report that mono-olein/taurocholate or oleic acid/taurocholate promotes the absorption of heparin, which is poorly absorbed when administered alone. Taniguchi, K. et al., *International Journal of Pharmaceutics*, 4: 219 (1980). Absorption of heparin from the large intestine was twice that which occurred from the small intestine. The concentration of heparin in the mixed micelle to produce the potentiation in the large intestine was approximately one-fourth that required in the small intestine.

In U. S. Pat. No. 4,156,719, Sezoshi and Muranishi describe a micelle solution for rectal administration of water-soluble drugs that are poorly absorbed. The composition consists of fatty acids having 6–18 carbons, and/or mono- or di-glycerides having the same type of fatty acids; a bile salt or other non-ionic surface active agent; and water. A lysophosphatidyl choline moiety can be substituted for the fatty acids and mono- or di-glycerides. Absorption of streptomycin and gentamycin from the rectum and large intestine is reported to be comparable when the drug is administered in a bile salt: mixed lipid micelle. Similar formulations were not effective in increasing absorption in the duodenum. Muranushi, S. et al., *International Journal of Pharmaceutics*, 2: 101 (1979). Absorption of the two drugs via the rectum and large intestine was markedly greater than that of a comparable dose administered duodenally, even when the mixed lipid micelle concentration administered duodenally was four times that administered via the other routes.

At the present time, there is a need for a more effective method of enhancing absorption of orally administered drugs from the small intestine. Much of a drug administered orally never reaches the targeted sites, either because the drug is poorly absorbed or because after it is absorbed, much is removed by the liver. If a more effective means were available to enhance the absorption of a drug, therapy would be more efficient because a smaller quantity of the drug would need to be administered to ensure that the desired amount would reach the target sites.

Nutrition

The caloric requirements of individuals are primarily a function of body composition and level of physical activity. Medically compromised, aged and physically stressed individuals often have limited body fat. Consequently, energy (caloric) needs will be satisfied mainly from exogenous sources.

Physical activity uses muscle and the energy requirements of all muscles, including the heart, are met primarily as a result of oxidation of fatty acids, from dietary fat or mobilized adipose fat. Adipose fat can, as noted, be minimal and therefore efficient absorption of fat can be an important consideration in satisfying the energy demands of the medically infirm, the aged and the physically active.

Fat absorption can be compromised in many circumstances. For example, in cystic fibrosis, a disorder of exocrine glands, there is a deficiency of pancreatic enzymes, bile salts and bicarbonate ions. *Nutrition Reviews*, 42: 344 (1984); Ross, C. A., *Archives of Diseases of Childhood*, 30: 316 (1955): Scow, R. 0. E., *Journal of Clinical Investigation*, 55: 908 (1975). Fat absorption in cystic fibrosis patients can be severely affected and 30 to 60 percent of ingested fat can be malabsorbed. The malabsorption and resulting steatorrhea are generally not successfully handled by the oral administration of pancreatic lipase. In an effort to control the steatorrhea, the patient may consume less fat than desirable for good health.

Fat absorption can be compromised under stressful conditions and the generally accepted way of addressing this problem has been to reduce fat consumption. This approach can result in both acute and chronic medical problems. These problems might be avoided, or at least minimized, if a readily absorbable source of fat could be made available.

DISCLOSURE OF THE INVENTION

The subject of this invention is a composition comprised of: 1) non-esterified fatty acids having 14–18 carbon atoms, 2) monoglycerides which are monoesters of glycerol and fatty acids having 14–18 carbon atoms, 3) lysophosphatidyl choline in which the fatty acid component has 14–18 carbon atoms, and 4) a drug. The non-esterified fatty acids and the esterified fatty acid moieties of the monoglycerides and the lysophosphatidyl choline can be unsaturated or saturated. In particular, the unsaturated fatty acids can be palmitoleic, oleic, linoleic or linolenic, which can be present in the composition individually or in combination. The saturated fatty acids, which also have 14–18 carbon atoms, can be, for example, myristic, palmitic or stearic.

The non-esterified fatty acids and the monoglycerides are present in the composition in a molar ratio of between about 2:1 and about 1:2 (non-esterified fatty acids:monoglycerides). The lysophosphatidyl choline comprises from about 1.0 mole % to about 30.0 mole % of the total composition.

If the non-esterified fatty acids in the composition are saturated, sufficient quantities of divalent cations (approximately one-half the molar amount of the fatty acids), such as calcium ions, are added to form non-esterified fatty acid salts.

The composition of this invention is designed to promote uptake of the mixed lipid colloid into the mucosa of the small intestine, subsequent synthesis into chylomicrons, translocation of the chylomicrons to the thoracic lymph and transport to the systemic circulation (i.e., blood).

The composition which is the subject of this invention will promote rapid and quantitative absorption of lipids in the small intestine and transport of lipids via the lymphatics because of several characteristics. First, the mole ratio described for the fatty acids and monoglycerides is optimal for their absorption in the jejunum. Second, the unsaturated fatty acids or saturated fatty acid-calcium salts included in the composition have been shown to be maximally absorbed and preferentially transported via the thoracic lymph (and not transported via the portal blood). Third, the composition also contains lysophosphatidyl choline, which enhances translocation of the reconstituted lipids as chylomicrons into the thoracic lymph.

The composition which is the subject of this invention can serve as a vehicle for enhanced uptake and bioavailability of drugs. Drugs are broadly defined here as any chemical agents or chemical substances which affect living processes. Examples of substances which can be incorporated into the composition of this invention are drugs administered for diagnostic, therapeutic or preventive purposes; lipophilic pro-drugs; bioactive peptides; some nutrients, such as fat-soluble vitamins, and other xenobiotics. This enhancement occurs because the substance incorporated into the composition of this invention is absorbed along with the lipids and subsequently enters the systemic circulation via the lymphatics. As a result, it is absorbed more rapidly and more completely than it otherwise would be. Because first pass clearance by the liver is avoided, more of the absorbed dose enters the blood and is available to reach target sites than would be available if the lipid formulation were not used.

The subject composition can also serve as a highly concentrated source of readily absorbable fat, which can be used, for example, by those in need of a calorically dense dietary component. When used in this manner, the composition of the present invention is comprised of 1), 2) and 3) as described above and does not include a drug.

The subject composition also provides a stable mixed lipid colloid that will protect the drugs from, for example, enzymatic and chemical degradation in the stomach and upper intestine. In addition, the inherent stability of the lipid components will make the compositions stable over extended periods and thus can serve as stable delivery vehicles for the substances incorporated into the formulation.

DETAILED DESCRIPTION OF THE INVENTION

Figure 1:
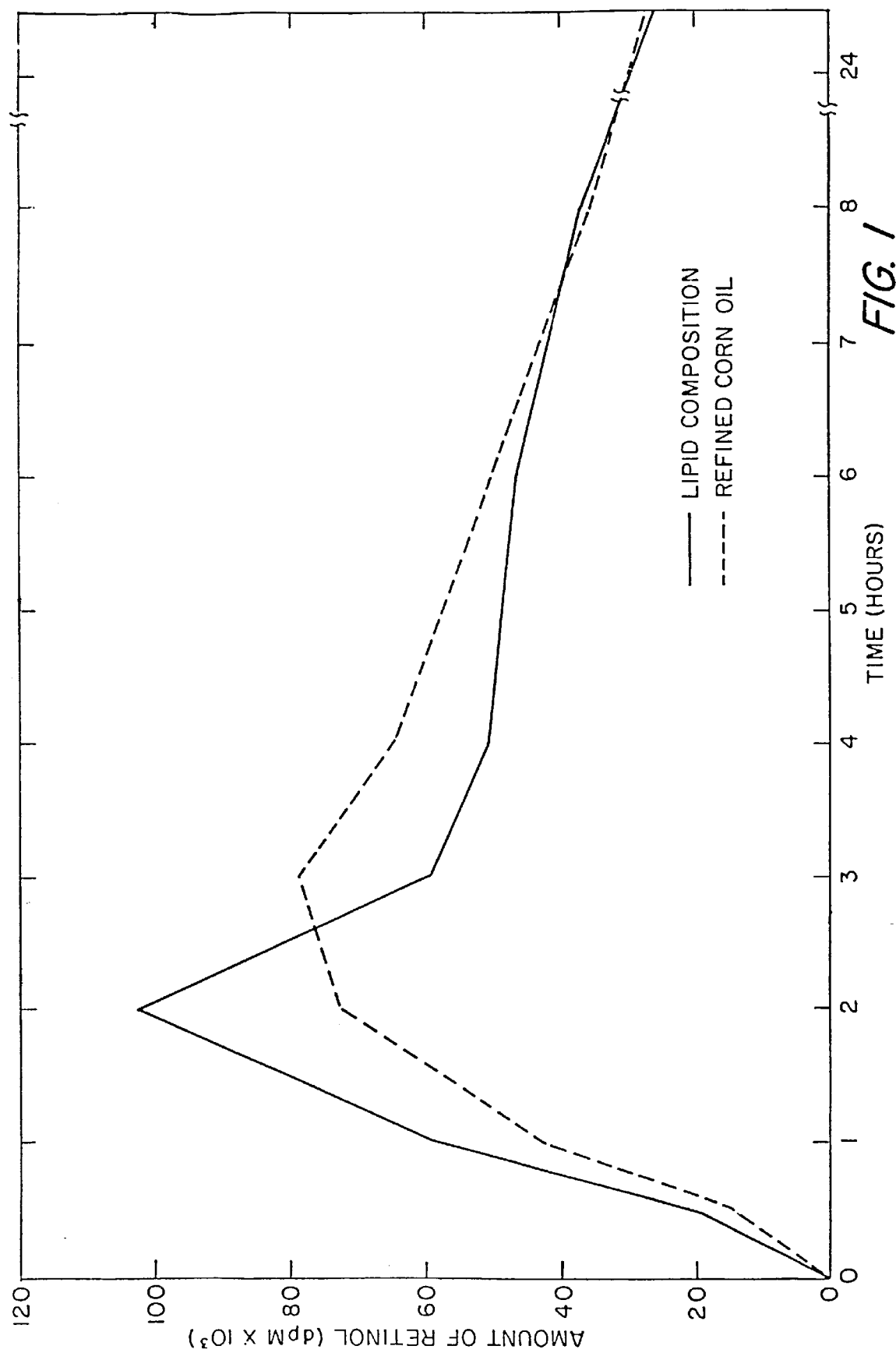
FIG. 1 is a graph showing the total vitamin A-derived radioactivity equivalents over time in plasma of rats given $^3$H-vitamin A in a composition and in plasma of rats given $^3$H-vitamin A in corn oil.

The composition of the present invention, which is comprised of non-esterified fatty acids, monoglycerides of those fatty acids, lysophosphatidyl choline having those fatty acids as their fatty acid moiety, and a drug is based on the absorption and transport characteristics of the fatty acids and the contribution of lysophosphatidyl choline to solubilization of the drug in the lipid composition and to translocation of absorbed fat into the lymph (rather than into the portal circulation).

Hydrolysis of triglycerides yields a molar ratio of fatty acids to monoglyceride of 2:1. In subsequent absorption and resynthesis in the intestinal muscosa, dietary fatty acids are mixed and lose their identity; new triglycerides, partly characteristic of the species, are formed.

Two constituents of bile are fatty acids and phosphatidyl choline. Enzymatic hydrolysis of phosphatidyl choline yields fatty acids; complete hydrolysis produces two molecules of fatty acid and partial hydrolysis produces one molecule of fatty acid and lysophosphatidyl choline. As a result, a composition having an excess of monoglyceride (e.g., fatty acid:monoglyceride ratio of 1:2) can equilibrate with those fatty acids derived from bile to approximate the optimum ratio of 2:1 for the enhanced absorption of mixed lipid colloids from the upper intestine. A ratio of fatty acid: monoglycerides which is not within this range (i.e., 1:2 to 2:1) may not enhance lipid absorption. It may also compromise not only lipid absorption, but also co-absorption of drugs administered with the lipids. A less effective means of accomodating the excess fatty acids is the addition of glycerol in place of monoglycerides. If the component lipids are not absorbed within the jejunal region of the intestine, they progress along the small intestine to the large intestine. The drugs which migrate with the lipids may be absorbed and transported via the portal blood for first pass clearance by the liver. Once in the large intestine, the component lipids are utilized by the intestinal microflora. These microorganisms may also metabolize the drug co-migrating with the component lipids to produce toxicologically-active species. Goldman, P. In: *The Molecular and Cellular Approaches to Understanding the Mechanisms of Toxicity*, A. H. Tashjian (ed.) 164, (1983).

Absorption of saturated fatty acids has been shown to be inversely related to the number of carbon atoms in the fatty acid. For example, absorption of decanoic (10:0, which denotes chain length and degree of unsaturation) is almost quantitative. For lauric (12:0), it is more than 95%; for myristic (14:0), 80–90%; for palmitic (16:0), 65–70% and for stearic (18:0), 30–45%.

Transport of absorbed fatty acids via the lymph (and not in the portal circulation) varies greatly. That is, a much larger percentage of absorbed unsaturated fatty acids has been shown to be carried in the lymph than is the case for saturated fatty acids. About 85% of unsaturated fatty acids has been shown to be carried in the lymph. Miura, S. et al., *Keio Journal of Medicine,* 28: 121 (1979). In contrast, 5–20% of absorbed decanoic (10:0) and 15–55% of absorbed lauric (12:0) is transported in the lymph, even though 95% of a given quantity of each will be absorbed. The remainder is absorbed into the portal blood. As noted above, the percent absorption of saturated fatty acids is inversely related to chain length. That is, myristic (14:0) is absorbed to a greater extent than is palmitic (16:0), which in turn is absorbed to a greater extent than is stearic (18:0). The amount of these absorbed fatty acids being carried in the lymph is also inversely related to chain length: 68–80% for myristic; 85% for palmitic and stearic. In addition, unsaturated fatty acids (e.g., linoleic 18:2) have been shown to be absorbed into lymph more rapidly and to a greater extent than are saturated fatty acids. Taniquchi, K., *International Journal of Pharmaceutics,* 4: 219 (1980).

If saturated fatty acids are included in the composition of this invention, they are included as calcium salts or salts of another cation. This is true because the enzymatic hydrolysis of triglycerides, which releases saturated fatty acids, favors their calcium soap formation. Tak, Y. A. and Grigor, M. R., *Biochimica Biophysica Acta,* 531: 257 (1978).

Translocation of absorbed fat into the lymph has been shown to require lysophosphatidyl choline. Lysophosphatidyl choline and phosphatidyl choline both contain phosphoryl choline linked to C-1 of glycerol, but differ in the number of fatty acids they contain. Lysophosphatidyl choline has a single fatty acid component located at either C-1 or C-2 of the molecule; phosphatidyl choline has two fatty acid moieties (one at C-1 and one at C-2). The rate, but not the magnitude, of the translocation of absorbed fat is apparently related to the fatty acid moiety of the lysophosphatidyl choline. For example, oleoyl lysophosphatidyl choline (derived from di-oleoyl phosphatidyl choline) results in a 100% increase in triglyceride and phospholipid in lymphatic transported fat when compared with the effects of a lysophosphatidyl choline derived from a phosphatidyl choline composed mainly of saturated fatty acids (e.g., palmitic, C16:0; stearic, C18:0). In the absence of luminal phosphatidyl choline to yield a lysophosphatidyl choline, there is an increased accumulation of mucosal triglyceride and apparently increased portal transport of the absorbed fatty acids. Tso, P et al., *Gastroenterology,* 80: 60 (1981); O'Doherty, P. J. A. et al., *Lipids,* 8: 249 (1973). If the fat load is increased five fold, a deficiency in lymphatic transport of absorbed fat becomes apparent. This effect is remedied by the addition of a source of lysophophatidyl choline. Tso, P. et al., *Gastroenterology,* 73: 1362 (1977). This effect by lysophosphatidyl choline which is observed in vivo is also apparent in vitro. Rodgers, J. B., and O'Connor, P. J., *Biochimica Biophysica Acta,* 409: 192 (1975). It has been shown that lysophosphatidyl choline is rapidly absorbed intact. Rodgers, J. B. et al., *Digestive Diseases,* 20: 208 (1975); Nilsson, A., *Biochimica Biophysica Acta,* 137: 240, (1976). Lymphatic phospholipids have also been shown to contain mainly unsaturated fatty acids: oleic (18:1), 50 to 63%; linoleic (18:2), 17 to 20%; and arachidonic (20:4), 2 to 4%. Incorporating an unsaturated lysophosphatidyl choline into the composition of this invention will enhance the translocation of the absorbed lipids and the co-absorbed drugs or other substances. In addition, lysophosphatidyl choline plays a role in the solubilization of some drugs (i.e., its presence enhances the solubility of the drugs in the composition).

The composition of this invention is comprised of non-esterified fatty acids having 14–18 carbon atoms; monoglycerides which are monoesters of glycerol and fatty acids having 14–18 carbon atoms; lysophosphatidyl choline in which the fatty acid moiety also has 14–18 carbon atoms, and a drug. The non-esterified fatty acids and the fatty acids of the monoglycerides and the lysophosphatidyl choline can be unsaturated or saturated and preferably will be unsaturated. Examples of unsaturated fatty acids which can be used in the composition of this invention are:

| palmitoleic | $C_{16}H_{30}O_2$ | 16:1 |
| oleic | $C_{18}H_{34}O_2$ | 18:1 |
| linoleic | $C_{18}H_{32}O_2$ | 18:2 |
| linolenic | $C_{18}H_{30}O_2$ | 18:3 |

Examples of saturated fatty acids which can be used in the subject composition are:

| myristic | $C_{14}H_{28}O_2$ | 14:0 |
| palmitic | $C_{16}H_{32}O_2$ | 16:0 |
| stearic | $C_{18}H_{36}O_2$ | 18:0 |

The non-esterified fatty acids and monoglycerides are present in amounts which result in a molar ratio of from about 2:1 to about 1:2 (non-esterified fatty acid:monoglyceride).

In addition, the composition has lysophosphatidyl choline, the fatty acid moiety of which has 14–18 carbon atoms and is preferably unsaturated. The fatty acid constituent of the lysophosphatidyl choline is preferably one of those listed above. The quantity of lysophosphatidyl choline in the composition is determined by the amount needed for enhanced solubilization of a drug to be administered in the composition and the amount needed for its role in translocation. In general, lysophosphatidyl choline comprises from about 1.0 mole % to about 30.0 mole % of the total composition. The fatty acids which comprise the composition of this invention—whether as non-esterified fatty acids or as constituents of monoglycerides or lysophosphatidyl choline—can all be the same or a number of different ones can be included.

The composition of the present invention also comprises a drug, which can be any chemical agent or chemical substance which affects living processes. They include, but are not limited to drugs administered for diagnostic, therapeutic or preventive purposes; lipophilic pro-drugs; some nutrients, such as fat soluble vitamins, and other xenobiotics.

The composition of this invention is made according to the following method. The component lipids are weighed and mixed, with or without heat, to attain liquid homogeneity. The drug is added and dissolved, with or without heat, in the lipid mixture. A uniform state is indicated by the absence of any solids at the appropriate temperature for the mixture to be a liquid and the absence of any schleirin. A schleiric effect will be more apparent at greater concentrations of the drug in the lipid mixture. The formulation is stable to several freeze-thaw cycles; the appearance of solids or schleirin may indicate instability of the formulation.

A second method of making the formulation involves dissolving the component lipids and drug in a solvent or mixture of solvents and mixing to attain homogeneity. The solvents are removed, in vacuo or by other suitable methods. The criteria for a suitable formulation will be the same as noted above.

The composition of this invention is illustrated by the following examples.

EXAMPLE I

Preparation of Composition and Comparison with Corn Oil as a Delivery Means

Lipid Composition

Tritium labeled ($^3$H) vitamin A (7 mg or 0.25 millimoles; 30 curies per mole; specific activity 1.26 mC/mmole; Hoffman LaRoche) was incorporated into a lipid formulation of the following composition: 56 mg. of oleic acid (NuCheck Prep, Inc.); 36 mg. of mono-olein (NuCheck Prep, Inc.) and 6 mg. of lysophosphatidyl choline derived from soy lecithin (A. E. Staley Mfg. Co.). This corresponds to an approximate molar ratio of oleic acid: mono-olein: lysophosphatidyl choline of 2:1:0.1. (The approximate molar percentages of the components were 64.5:32.3:3.2, respectively). The composition was administered to Sprague-Dawley rats (weighing 210–230 gm) by gavage.

Corn Oil Preparation

Tritium-labeled vitamin A (7 mg. or 0.25 milli-moles) was administered to Sprague-Dawley rats (as above) in 99 mg. food grade, refined corn oil (A. E. Staley Mfg. Co.).

Experimental Procedure and Results

The concentration of vitamin A equivalents in the plasma was measured by obtaining duplicate 0.05 ml. blood samples from the orbital sinus at 0.5, 1, 2, 3, 4, 6, 8 and 24 hours after administration. The blood was collected in hematocrit tubes and centrifuged; the plasma was transferred into tared scintillation vials and weighed. The radioactivity was determined by liquid scintillation counting.

Results indicated a slow absorption of the vitamin A over an 8 hour period (FIG. 1). An estimate of the amount that was absorbed as a function of time is shown in Table 1. About 73% of the vitamin A in the composition was absorbed within 2 hours after administration; approximately 50% of the vitamin A administered in corn oil was absorbed in the first 2 hours. At 3 hours after administration, more than 90% of the vitamin A in the lipid composition and 77% of that in the corn oil had been absorbed.

At the end of the 8-hour study period, absorption of vitamin A in both the composition and the corn oil was complete. The plasma concentration of tritiated vitamin A equivalents in rats in the two groups were comparable. The composition enhanced absorption of the vitamin A incorporated into it and also caused the vitamin to be absorbed more quickly.

The areas under the concentration-time curve for the 8 hour period were also equivalent, indicating that the absorption of vitamin A in the composition was quantitative. In a similar comparison, some 73% of the vitamin A in the composition was absorbed within 2 hours (Table 1) and was greater than 90% at 3 hours as compared to 52 and 77% for vitamin A, administered in corn oil. Thus it is apparent that the composition will provide for both the enhanced and earlier absorption of incorporated drugs and, therefore, enhance their effectiveness.

TABLE 1

Percent Absorption of Vitamin A Administered in the Composition or in Corn Oil to Rats by Oral Intubation

| Hours | Percent Absorption | | Ratio |
|---|---|---|---|
| | Lipid Composition | Corn Oil | Composition/Oil |
| 0–0.5 | 5.4 | 4.0 | 1.35 |
| 0.5–1 | 27.3 | 20.0 | 1.37 |
| 1–2 | 72.6 | 52.4 | 1.39 |
| 2–3 | 92.0 | 77.2 | 1.19 |
| 3–4 | 97.3 | 91.8 | 1.06 |
| 4–6 | 100. | 99.5 | 1.01 |
| 6–8 | 100. | 100. | 1.00 |

EXAMPLE II

Estimation of Capacity and Stability of a Composition as a Vitamin A Delivery Means A composition that included oleic acid, mono-glyceride and lysophosphatidyl choline as described in Example I was used for characterizing the capacity of the composition for vitamin A (also as described above). Vitamin A was added in batches to the composition as follows: 1st addition, 0.277 mmoles; 2nd, 0.241; 3rd, 0.276; 4th, 0.262 and 5th, 0.285. The 5th addition resulted in the addition of 1.34 mmoles or 384 mg of vitamin A to approximately 1 gm of the composition. The millimole ratio of the composition was approximately 2:1:0.1 (oleic acid: mono-olein:lysophosphatidyl choline).

After each addition the approximate amount of time necessary for the complete dissolution of the added vitamin A was recorded, as was the extent of schlierin evident. The time needed to obtain a minimal schlieric effect was generally between 5 minutes and 60 minutes and inversely related to the amount of vitamin A added. After each addition and the achievement of a minimal schlieric effect, the solution was placed in an ice-bath in order to evaluate its stability. The relative viscosity of the cold solution was also recorded. These findings are summarized in Table 2.

A clear solution, without schleirin, was observed within an hour after the 5th addition. The same solution was frozen for one week and thawed. A clear solution was observed at that time. This freeze-thaw cycling was repeated four times over an 8-week period with comparable results. Thus it is apparent that this lipid formulation is stable over extended periods of storage and changes in temperature.

TABLE 2

The Capacity of the Composition for Vitamin A

| Vitamin A | | Condition to Attain A Clear Solution | | | |
|---|---|---|---|---|---|
| Added (mmoles) | Total (mmoles) | Time | Temp. | Schleirin | Viscosity |
| 0.277 | 0.277 | 1 min. | 20° C. | none | normal |
| 0.241 | 0.518 | 1 min. | 20° C. | minimal | normal |
| 0.276 | 0.794 | 5 min. | 37° C. | medium | thicker |
| 0.262 | 1.056 | 10 min. | 37° C. | medium | viscous |
| 0.285 | 1.341 | 10 min. | 46° C. | extensive | very viscous |

EXAMPLE III

Estimation of Solubility of N-(4-Hydroxyphenyl)-All-Trans-Retinamide (HPR) in Lipid Formulations Lipid Formulations N-(4-Hydroxyphenyl)-all-trans-retinamide (HPR) (McNeil Pharamceutical) was used for characterizing its solubility in several formulations of the composition of the present invention. The make up of the composition varied with respect to the fatty acid constituents among the three basic components: fatty acid (NuCheck Prep Inc.), monoglyceride (NuCheck Prep Inc.), and lysophosphatidyl choline (Avanti Polar Lipids). The formulations used are listed in Table 3.

In each formulation, the lipid components were first mixed together in a sealed container under nitrogen. Solid HPR was added in increments. After each addition, the container was resealed under nitrogen and heated and sonicated to produce a solution of the HPR or until it became apparent that the solid HPR would remain in suspension. Those formulations which resulted in solution of HPR were refrigerated or frozen and the continued solubilization of the HPR was noted. In all instances, the HPR, once solubilized, did not precipitate out of the solution.

The results of observations for the formulations are shown in Table 3. In formulations II and III, solution of HPR was noted when the molar ratio of the lysophosphatidyl choline (LysoPC) to HPR (LysoPC:HPR) was greater than unity; a suspension of HPR was observed when the molar ratio of lysophosphatidyl choline to HPR was less than unity. In comparing formulations III and IV, which contained approximately the same amount of HPR, the LysoPC:HPR ratio was less than unity in formulation III when a suspension of HPR was observed and greater than unity in formulation IV when a solution was apparent. Comparison of formulations V and VI showed that the solution of HPR was apparent at molar ratio of 1 (LysoPC:HPR) for the lysophosphatidyl choline containing either the fatty acid myristoyl (14:0) or palmitoyl (16:0). In formulation V, the solubilization of the third sequential addition of HPR appeared to be more difficult than the first two additions. This is a further indication of the importance of having a molar ratio of LysoPC:HPR greater than 1.

Formulation VII represented a formulation of HPR that contained all the components of the previous formulations. As described in Example IV, it was administered to dogs. Briefly, the ratio of 18:1 LysoPC:HPR was 0.69; the ratio of 14:0 Lyso-PC:HPR was 0.33; and the ratio of 16:0 LysoPC:HPR was also 0.33. The molar ratio of lysophosphatidyl choline:HPR in Formulation VII was 1.31:1.

Dogs received food and water ad-lib during Treatment A and Treatment $E_2$. They were food-fasted for 12 hours before receiving Treatment $E_1$; the fasting continued until two hours after dosing.

Figure 2:
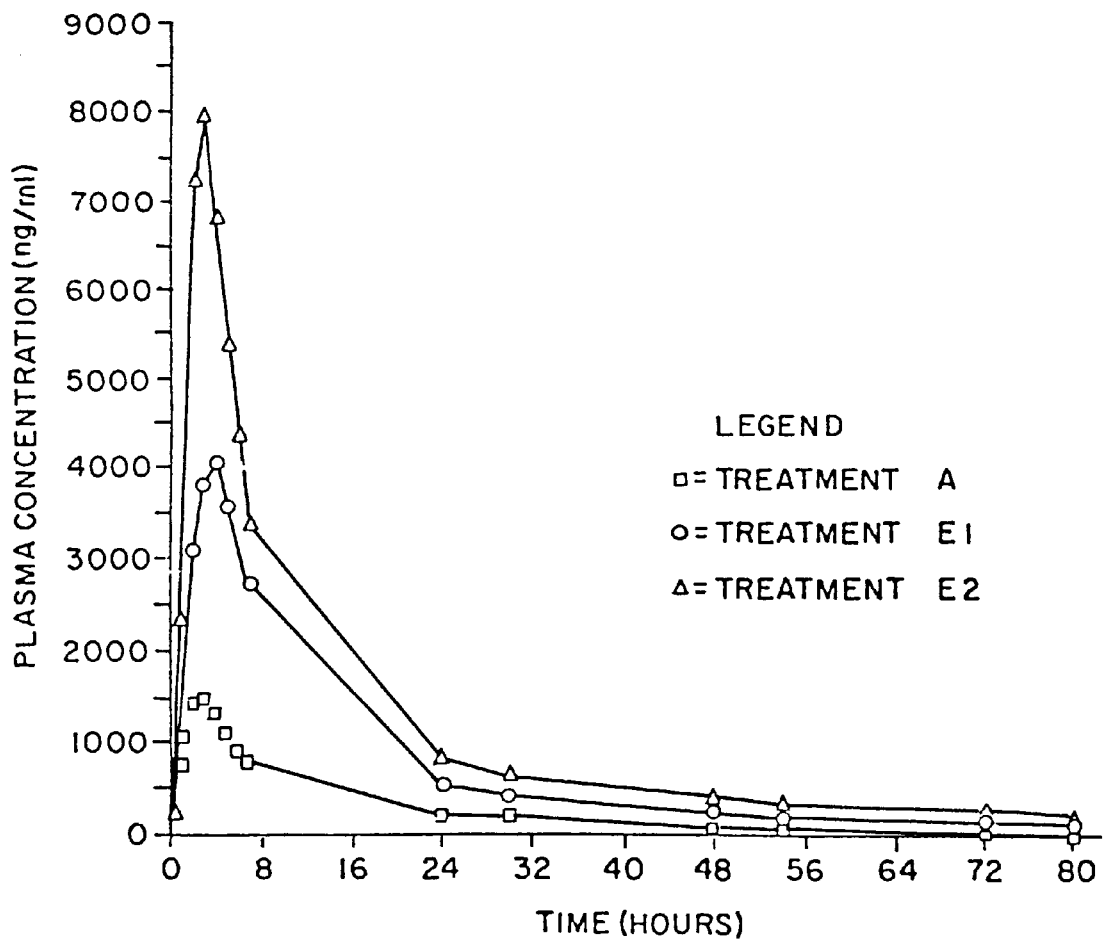
FIG. 2 is a graph showing the mean plasma concentration-time profiles of N-(4-Hydroxyphenyl)-all-trans-retinamide (HPR) in dogs following oral administration of HPR.

Plasma samples were analyzed for HPR by a high pressure liquid chromatography procedure. Plasma concentration of HPR in this study are summarized in Table 4 and FIG. 2.

Mean peak HPR concentrations were 1660, 4238 and 8174 ng/ml for Treatment A, $E_1$ and $E_2$, respectively (Table

TABLE 3

Solubility of HPR in Lipid Formulations

| Formulation Number | Lipid Formulation | | | Addition of HPR | | | Sequential Observation After HPR Additions |
|---|---|---|---|---|---|---|---|
| | Constituent | mg | mmoles | Sequence Number | mg | Cummulative mmoles | |
| II | 18:1 FA | 667 | 2.364 | 1. | 10.3 | 0.026 | 1. Solution |
| | 18:1 MG | 358 | 1.004 | 2. | 30.6 | 0.104 | 2. Suspension |
| | 14:0 LysoPC | 49 | 0.096 | | | | |
| III | 18:1 FA | 575 | 2.038 | 1. | 22.1 | 0.056 | 1. Solution |
| | 18:1 MG | 356 | 0.9997 | 2. | 35.7 | 0.147 | 2. Suspension |
| | 18:1 LysoPC | 92 | 0.0998 | | | | |
| IV | 18:1 FA | 473 | 1.680 | 1. | 32.2 | 0.082 | 1. Solution |
| | 18:1 MG | 303 | 0.850 | 2. | 37.9 | 0.179 | 2. Solution |
| | 18:1 LysoPC | 144 | 0.277 | | | | |
| V | 18:1 FA | 476 | 1.689 | 1. | 51.9 | 0.132 | 1. Solution |
| | 18:1 MG | 300 | 0.844 | 2. | 20.8 | 0.186 | 2. Solution |
| | 14:0 LysoPC | 128 | 0.278 | 3. | 30.3 | 0.263 | 3. Solution |
| VI | 18:1 FA | 568 | 2.015 | 1. | 73.1 | 0.187 | 1. Solution |
| | 16:0 MG | 333 | 1.007 | 2. | 51.3 | 0.318 | 2. Solution |
| | 16:1 LysoPC | 160 | 0.318 | | | | |
| VII | 18:1 FA | | 25.720 | 1. | 16.004 | 4.087 | 1. Solution |
| | 18:1 MG | | 9.594 | | | | |
| | 16:0 MG | | 3.198 | | | | |
| | | | 12.792 | | | | |
| | 18:1 LysoPC | | 2.806 | | | | |
| | 14:0 LysoPC | | 1.279 | | | | |
| | 16:0 LysoPC | | 1.271 | | | | |
| | | | 5.356 | | | | |

EXAMPLE IV

Bioavailability of N-(4-Hydroxyphenyl)-All-Trans Retinamide (HPR) Administered in a Formulation The study was designed to compare the bio-availability of HPR from the lipid formulation VII (see Example III and Table 3), administered to beagle dogs under fasting (Treatment $E_1$) and fed (Treatment $E_2$) conditions with the bioavailability of HPR administered to Beagle dogs in a reference formulation (Treatment A) under fed conditions. The reference formulation was an oil-based composition containing a surfactant. Four beagle dogs were used in these studies; all dogs received HPR with at least one week between treatments. The dose of HPR for treatment A and $E_1$ was 200 mg; it was administered in suspension in treatment A and in solution in Treatment $E_1$, and in each case was administered as two 100 mg capsules. In Treatment $E_2$, 100 mg of HPR in solution was administered as one 100 mg capsule. All the data for Treatment $E_2$ are presented with normalization to a 200 mg dose.

4). The mean area under the curve, AUC (0–80 hr) values were 22666, 62590 and 95935 ng.hr/ml for Treatment A, $E_1$ and $E_2$, respectively (Table 5). It is readily apparent that the bioavailability of HPR administered in Formulation VII (Treatment $E_1$ and $E_2$) was greater than the bioavailability of HPR administered in the reference formulation (Treatment A). Comparison of results obtained when Formulation VII was administered to animals in the fed state ($E_1$) with results obtained when the formulation was fed to fasted animals ($E_2$) indicates that additional lipids (from foods consumed) resulted in a further increase in AUC (1.5 fold increase between Treatment $E_2$ and $E_1$). The unsaturated lysophosphatidyl cholines are particularly useful for translocation of absorbed fat into the lymph. Since these unsaturated lysophosphatidyl cholines may have been associated with the HPR, there was insufficient 18:1 lysoPC for both solubilization of the HPR and translocation of the absorbed lipids and HPR into the lymph. Consequently, those drugs which interact with the lysophosphatidyl choline in the lipid formulation apparently require a greater mole ratio of lysophosphatidyl choline with respect to fatty acids and monoglycerides.

TABLE 4

Summary of Plasma Concentration-Time Data of HPR in Four Dogs Following the Oral Administration of HPR in Formulation VII Mean HPR Concentration In Plasma - ng/ml

| Formulation State<br>Time (Hours) | Reference A<br>Fed | Lipid-$E_1$<br>Fasted | Lipid-$E_2$[a]<br>Fed |
|---|---|---|---|
| | Plasma HPR Concentration (ng/ml) | | |
| 0 | .0 | 24.0 | 121.9 |
| 0.5 | 219.9 | 238.9 | 345.5 |
| 1 | 769.7 | 1093.3 | 2388.3 |
| 2 | 1430.6 | 3124.7 | 7259.8 |
| 3 | 1490.5 | 3866.0 | 8032.5 |
| 4 | 1325.2 | 4078.8 | 6841.1 |
| 5 | 1105.2 | 3599.1 | 5411.0 |
| 6 | 914.3 | 3021.3 | 4386.7 |
| 7 | 797.3 | 2740.7 | 3402.7 |
| 24 | 187.4 | 557.5 | 852.6 |
| 30 | 198.0 | 426.5 | 646.1 |
| 48 | 93.9 | 253.3 | 449.3 |
| 54 | 79.4 | 193.6 | 333.9 |
| 72 | 69.7 | 149.0 | 276.0 |
| 80 | 47.8 | 114.5 | 210.3 |

[a] Corrected to Base Dose of 200 mg.

TABLE 5

Area under the Plasma Concentration-Time Curve [AUC (0–80 hr)] of HPR in Four Dogs Following the Oral Administration of HPR in Formulation VII HPR-AUC (ng H/ml)

| Formulation State | Reference A<br>Fed | Lipid-$E_1$<br>Fasted | Lipid-$E_2$[a]<br>Fed |
|---|---|---|---|
| Dog # | | | |
| 1 | 28609 | 50044 | 107106 |
| 2 | 15964 | 84898 | 127589 |
| 3 | 21190 | 78476 | 56274 |
| 4 | 24900 | 36941 | 92721 |
| Mean | 22666 | 62590 | 95935 |
| S.D. | 5398 | 22842 | 30054 |
| Median | 23045 | 64260 | 99939 |
| G Mean | 22156 | 59241 | 91905 |
| As a % of A | | | |
| Mean | | 276 | 423 |
| Median | | 279 | 434 |
| G Mean | | 267 | 415 |

[a] Corrected to a base dose of 200 mg.

Industrial Applicability

The composition of this invention has industrial applicability in the delivery of orally administered drugs or other substances. It can also serve as a readily absorbed source of energy from fat.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A nonaqueous composition for oral administration to an individual, comprising:

a. at least one non-esterified fatty acid having 14–18 carbon atoms;

b. at least one monoglyceride which is a monoester of glycerol and a fatty acid having 14–18 carbon atoms;

c. lysophosphatidyl choline in which the fatty acid moiety has 14–18 carbon atoms; and d. a drug, the mole ratio of the monoglyceride to fatty acid ranging from approximately 2:1 to approximately 1:2 and the mole ratio of lysophosphatidyl choline to the sum of monoglycerides and fatty acid ranging from approximately 1:3 to approximately 1:12., wherein said drug is solubilized in the fatty acid, monoglyceride, lysophosphatidyl choline combination.

2. A nonaqueous composition for increasing absorption of a fat-soluble drug in the lymphatics of an individual comprising:

a. non-esterified fatty acids having 14–18 carbon atoms;

b. monoglycerides which are monoesters of glycerol and a fatty acid having 14–18 carbon atoms.

c. lysophosphatidyl choline in which the fatty acid moiety has 14–18 carbon atoms; and d. a fat-soluble drug, the lysophosphatidyl choline being present in the composition in an amount sufficient for solubilization of said drug in the composition and the mole ratio of lysophosphatidyl choline to the sum of monoglyceride and fatty acid ranges from approximately 1:3 to approximately 1:12, wherein said fat-soluble drug is solubilized in the fatty acid, monoglyceride, lysophosphatidyl choline combination.

* * * * *